United States Patent [19]
Hayes et al.

[11] Patent Number: 5,092,864
[45] Date of Patent: Mar. 3, 1992

[54] METHOD AND APPARATUS FOR IMPROVED LASER SURGERY

[75] Inventors: Donald J. Hayes, Plano; J. Lester Matthews; Millard M. Judy, both of Dallas, all of Tex.

[73] Assignee: Microfab Technologies, Inc., Plano, Tex.

[21] Appl. No.: 516,661

[22] Filed: Apr. 30, 1990

[51] Int. Cl.⁵ ............................................. A61B 17/36
[52] U.S. Cl. ...................................... 606/10; 606/13; 606/16; 128/395
[58] Field of Search ............... 604/21; 606/2, 3, 7, 606/13, 14 15, 10–12, 16; 128/395–398, 633, 634, 664, 665; 219/121.6–121.62

[56] References Cited
U.S. PATENT DOCUMENTS

| | | | |
|---|---|---|---|
| 3,900,034 | 9/1975 | Katz et al. | 128/395 |
| 4,461,294 | 7/1984 | Baron | 128/395 |
| 4,832,024 | 5/1989 | Bonssignac et al. | 128/395 |
| 4,891,043 | 1/1990 | Zeimer et al. | 604/20 |

Primary Examiner—Stephen C. Pellegrino
Assistant Examiner—Steven J. Shumaker
Attorney, Agent, or Firm—Richards, Medlock and Andrews

[57] ABSTRACT

A method and apparatus for providing greater precision placement and control of the delivery of laser energy during laser surgery is disclosed and includes a pulse-controlled dye delivery system which may be coordinated with the delivery of laser energy to predetermined tissue. The pulse-controlled dye delivery system comprises at least one ejection head capable of ejecting drops of liquid dye with the diameter of each drop being less than two hundred microns. The dye is responsive to the wavelength of energy delivered by the laser performing the surgery to convert the laser energy from the surgical laser to tissue thermal energy. Circuitry is provided for precisely activating the dye delivery system and the laser energy source such that optimal conditions for successful outcome of the surgery may be achieved. Because of the small amount of dye deposited on the tissue and the very short time the dye is on the tissue before the laser energy arrives, the dye does not spread from the desired spot and concentrates the laser energy at the desired spot.

46 Claims, 2 Drawing Sheets

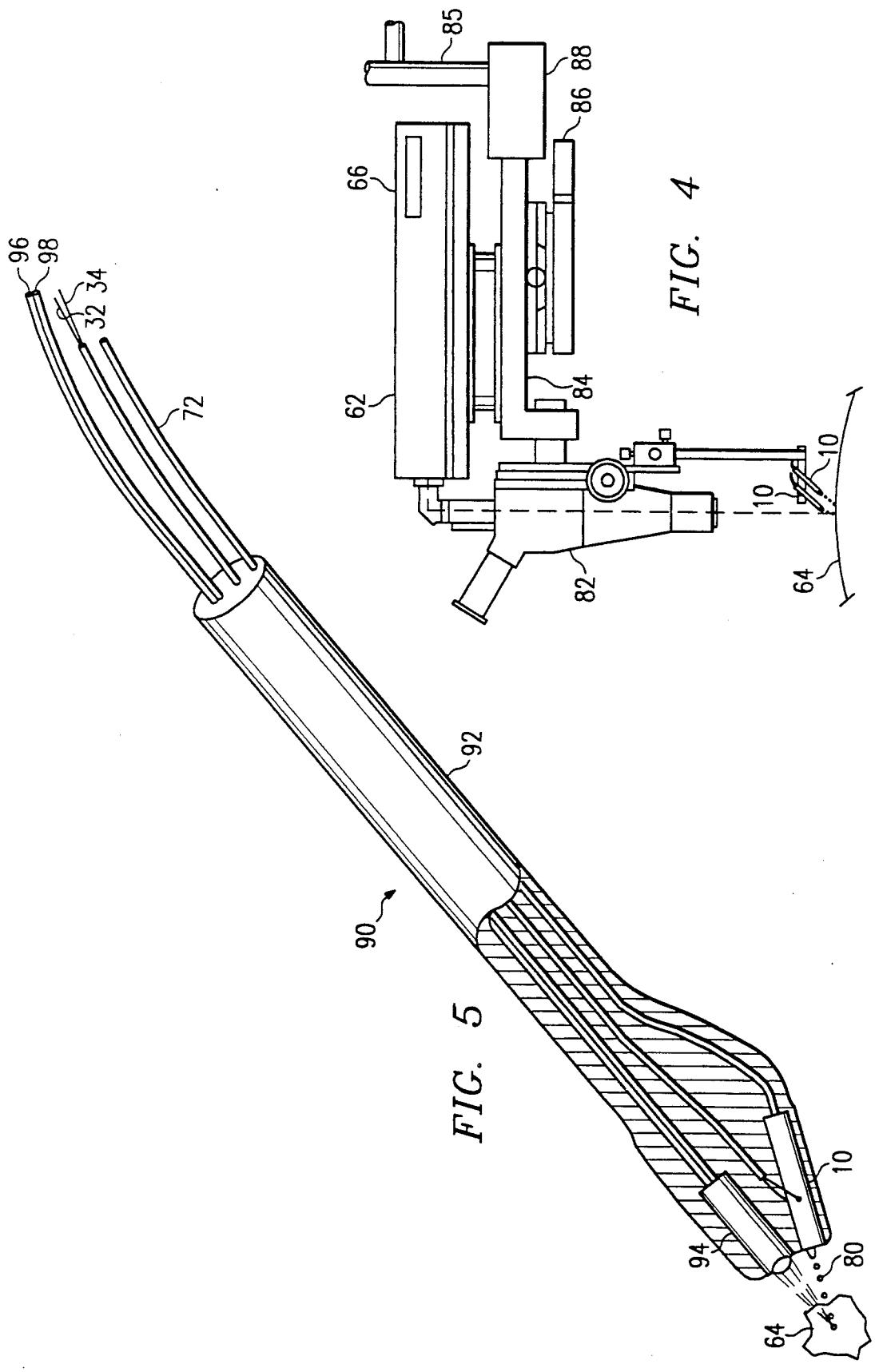

METHOD AND APPARATUS FOR IMPROVED LASER SURGERY

FIELD OF THE INVENTION

The present invention relates in general to laser surgery. More particularly, but not by way of limitation, it relates to a method and apparatus for the delivery of very small drops of dye to selected tissue locations to enhance the effect of laser energy delivered to the selected tissue locations stained by the very small drops of dye.

BACKGROUND OF THE INVENTION

Although this invention is applicable to the dispensing of very small and precise amounts of fluids to be used in conjunction with the dispensing of other fluids or quantities of energy, it has been found particularly useful in the environment of the delivery of very small drops of dye to enhance the effect of laser energy. Therefore, without limiting the applicability of the invention to "delivery of very small drops of dye to enhance the effect of laser energy", the invention will be described in such environment.

There are well known benefits from the use of surgical lasers in the medical field in the area of welding or closure of openings in tissue, for example, the coagulation of tissue to close an opening (ophthalmological vessel coagulation). There are also benefits from the use of a laser beam to ablate tissue to make an opening such as an incision or hole in tissue. The advantages of laser welding arise primarily from the avoidance of suture material which may distort the healing process and promote excessive scarring, a shorter operative time, a hemodynamically more perfect flow surface, etc.

It has been known in the medical field to use various dyes (also known as chromophores or materials which absorb light based upon their intrinsic optical junction properties) which absorb specific wavelengths of laser energy. These dyes could be materials which are naturally occurring, which are synthesized, etc.. Prior to the laser surgery, a line or painting of dye was laid down on the tissue where the cut or weld was to occur. The surgical laser was then activated and the energy therefrom was directed along the line or painting of dye. There were at least two problems with this method of operation. First, the line or painting laid down on the tissue was too wide for some applications and second, the time delay between the placing of the dye and the directing of the energy from the surgical laser allowed the dye to flow out over the tissue. This resulted in the laser energy being dispersed or spread-out from the intended line of tissue and requiring higher laser power to do the required surgery with a decrease in the accuracy of the work done by the laser energy.

It has also been known in the art of laser surgery and laser coagulation, that a CW beam of relatively low power of laser energy may be directed to the target tissue for relatively long periods of time and allow the thermal diffusion away from the impact site for the coagulation or welding effects. It is also known to provide a pulsed-type laser using very high peak pulse power to deliver the same total energy in pulsed form to produce coagulation. With the pulsed-type laser, the same total energy is delivered to the target tissue and coagulation only occurs at the impact site of the laser energy because there is not time for thermal diffusion to occur.

This invention effectively deals with these problems and allows greater accuracy in laser surgery with a laser of less power than was previously necessary for the same operation.

SUMMARY OF THE INVENTION

This invention provides a method and apparatus for improved laser surgery by providing for more precision placement and control of the delivery of laser energy and comprises a pulse-controlled dye delivery system which is coordinated with the delivery of laser energy to predetermined tissue. The pulse-controlled dye delivery system comprises at least one ejection head capable of ejecting drops of liquid dye through space with the diameter of each drop being less than two hundred microns. The dye is responsive to the wavelength of energy delivered by the laser performing the surgery to convert the laser energy from the surgical laser to tissue thermal energy. Means for activating the surgical laser and the ejection head includes means to control the relative activation of the surgical laser and the ejection head so the relative time of arrival of the drop or drops of dye and the laser energy to the predetermined tissue can be controlled and adjusted. CW (continuous wave) laser, shuttered CW laser and pulsed laser may be used with the ejection head to provide optimal conditions for the outcome of the surgery. The size of the drop or drops of dye can be adjusted to also optimize the conditions for the outcome of the surgery. In one embodiment, the surgery is performed with the aid of a microscope. In another embodiment, the surgery is performed with a hand-held unit which houses the ejection head, the surgical laser and the laser which provides a visible spot of light to indicate the location where the drop or drops of dye and the laser energy will contact the tissue.

BRIEF DESCRIPTION OF THE DRAWINGS

Other advantages and features of the invention will become more apparent with reference to the following detailed description of a presently preferred embodiment thereof in connection with the accompanying drawings, wherein like reference numerals have been applied to like elements, in which:

FIG. 4 is a simplified side elevational view of a surgical microscope including a low power laser, a surgical laser and two ejection heads for delivery of dye or another liquid that is constructed in accordance with the invention; and FIG. 5 is a simplified perspective view of a hand-held embodiment, with a portion thereof cut away, of the present invention.

DESCRIPTION OF THE PREFERRED EMBODIMENT

Figure 1:
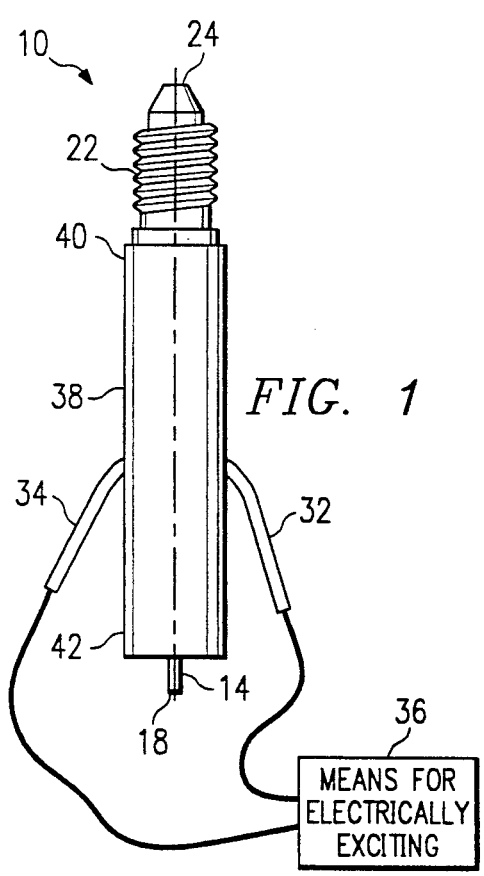
FIG. 1 is a simplified side elevational view of an ejection head of the present invention.
Figure 2:
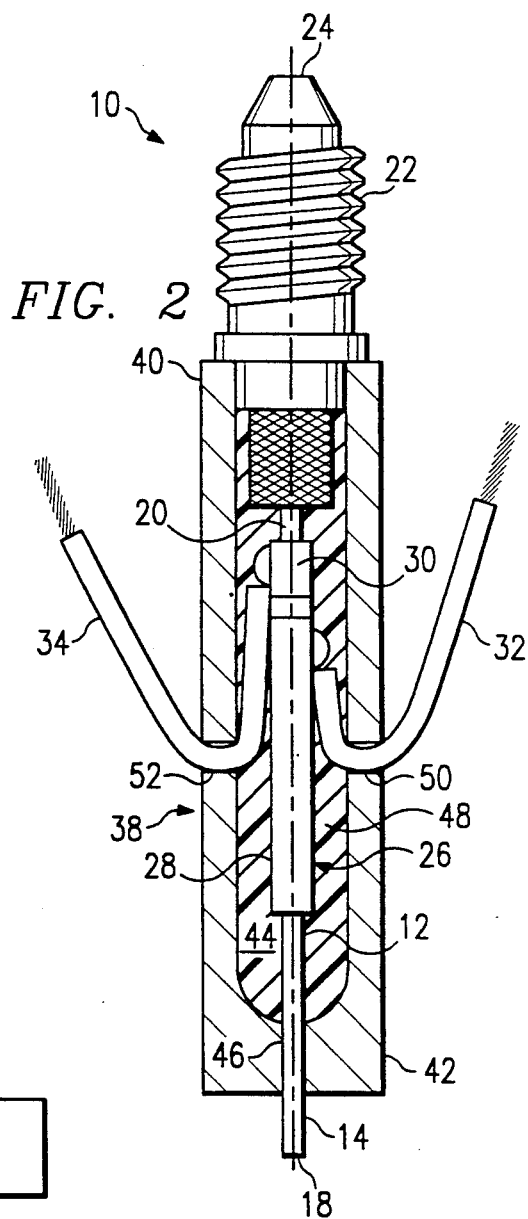
FIG. 2 is a simplified side elevational view of an ejection head of the present invention with portions thereof cut away.

Referring to the drawing and FIGS. 1 and 2 in particular, shown therein and generally designated by the reference character 10 is an ejection head or microjet for and capable of ejecting drops of liquid dye through space with the diameter of each drop being less than two hundred microns.

Ejection head or microjet 10 comprises a first housing 12 of predetermined length and predetermined diameter. First end 14 of first housing 12 is formed with an exit aperture 18 of less than two hundred microns in diameter. Second end 20 of first housing 12 is operatively connected to connector means 22. Connector means 22 is configured to allow tubing to be removably attached thereto for supplying liquid dye to first housing 12. It will be appreciated that aperture 24, which extends the length of connector means 22, is operatively connected to the second end 20 of first housing 12. In the preferred embodiment, first tubular housing 12 is tubular in shape and is formed from glass.

A driver device 26 structured in the form of a housing is positioned around first housing 12 and is positioned in operative contact therewith. Driver device 26 comprises an outer portion 28 and an inner portion 30, both of which are formed of a metallic substance. Electrical leads 32 and 34 are operatively connected to outer portion 28 and inner portion 30, respectively, and means for electrically exciting or activating 36 comprises means for providing electrical pulses together with interface electronics. Driver device 26 comprises any device for generating a pressure wave in first housing 12 to force a predetermined amount of liquid dye down the first housing 12 to exit aperture 18. In the preferred embodiment, driver device 26 comprises a piezoelectric device.

Second housing 38 has a first end 40 and a second end 42. Second housing 38 is positioned in a surrounding relationship to and coaxial with first housing 12 and is spaced therefrom to form a cavity 44 therebetween. First end 40 is operatively attached to connector means 22 while second end 42 is operatively attached to first end 14 of first housing 12 by adhesive material 46. Cavity 44 is filled with potting material 48 which is electrically insulative. Electrical leads 32 and 34 pass through apertures 50 and 52, respectively, in the wall of second housing 38. The primary purpose of second housing 38 is to protect first housing 12 from any external physical forces. In the preferred embodiment, second housing 38 is tubular in shape and is formed of a metallic or hard plastic material.

Figure 3:
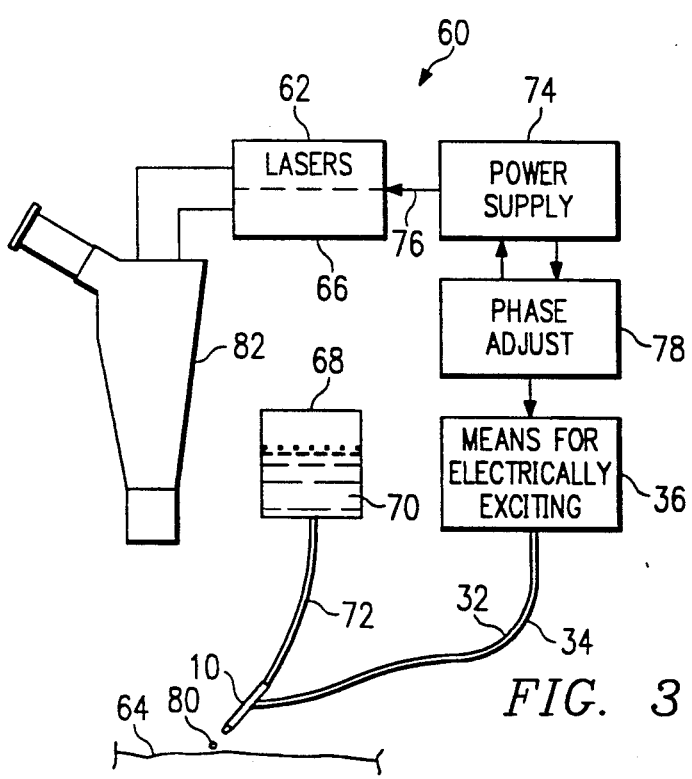
FIG. 3 is a simplified block diagram schematic showing the apparatus of the present invention.

With reference to FIG. 3, apparatus for improved laser surgery 60 is disclosed and comprises a low power laser 62 to deliver laser energy which provides a visible spot of light on tissue 64 (such as a human being) and a surgical laser 66 to deliver the laser energy which performs the surgery on tissue 64. The visible spot of light is used as a pointer so the surgeon will know the spot on the tissue 64 where the energy from the surgical laser 66 will be delivered when the surgical laser 66 is activated. The low power laser 62 and the surgical laser 66 are aligned such that the output of laser energy from each will converge on the same spot on tissue 64.

Ejection head or microjet 10 is operatively connected to reservoir 68 containing the liquid dye 70, or other liquid, by tubing 72 and to means for electrically exciting 36 by electrical leads 32 and 34. Power supply 74 supplies the necessary power and activation signals to low power laser 62 and the surgical laser 66 via cable 76. A synch output from power supply 74 is provided to a phase adjust circuit 78 whose outputs are provided to means for electrically exciting 36 and power supply 74. With controls on power supply 74 and phase adjust circuit 78 the sequence of exciting or activating surgical laser 66 and ejection head or microjet 10 and the time between their separate excitation or activation are adjustable.

It will be appreciated that the surgery could be performed using a microscope 82 with controls to move the low power laser 62 with its laser energy and therefore the visible spot of light as well as the ejection head or microjet 10 and the ejected drop 80 of liquid dye 70 and the laser energy from the surgical laser 66.

With reference to FIG. 4, one embodiment of the present invention is disclosed in an exemplary package including a microscope 82 and microscope support frame 84 including control means 86 and 88 for movement of microscope 82, low power laser 62 and the surgical laser 66 and support means 85 in the form of poles or rods connected to a ceiling support or floor support. Ejection heads or microjets 10 are also mounted on microscope stand 84 and are aligned such that a drop or drops 80 of liquid dye 70 or other liquid will be delivered through space to the tissue 64 where the visible spot of light is positioned which is also where the energy from the surgical laser 66 will be delivered. It will be appreciated that each ejection head or microjet 10 delivers a drop 80 of liquid dye 70, or other liquid, through space each time it is pulsed.

The second ejection head or microjet 10 may be used to deliver drops 80 of a second dye which has an optical absorption spectrum different than the dye in the first ejection head or microjet 10.

If the first ejection head or microjet 10 delivers drops 80 of a dye which has unique binding affinities for the tissue to be laser-affected, the second ejection head or microjet 10 could deliver a wash fluid to flush away the dye not absorbed by the tissue.

With reference to FIG. 5. another embodiment of the present invention is disclosed in a hand-held instrument 90 including housing 92, duel lens 94, ejection head or microjet 10 with leads 32 and 34, tubing 72 and fiber optics 96 and 98 to deliver the laser energy from the low power laser 62 and the surgical laser 66. This embodiment of the present invention would be used for less delicate and less precise surgery with the hand-held instrument 90 being held the correct distance from tissue 64 so the laser energy from the low power laser 62, the laser energy from the surgical laser 66 and the drop 80 of liquid dye 70 would converge and be delivered to the same location on tissue 64.

In operation of the invention, it is necessary to align the surgical laser 66 and each ejection head or microjet 10 such that their outputs converge at and are delivered at the location on the tissue 64 where the visible spot of light from the low power (pointer) laser 62 is positioned. The activation signal is initiated and the ejection head or microjet 10 and surgical laser 66 are activated in the desired sequence and desired time delay with the drop or drops 80 of liquid dye 70 enhancing the effect of the laser energy from the surgical laser 66. The visible spot of light is moved either by control means 86 and 88 or by hand (in the hand-held embodiment) to the next location and the sequence of activation is repeated. The entire sequence is repeated until the surgery is completed.

Some of the particular dye or dyes to be used with the present invention are materials which will absorb laser energy based upon their intrinsic optical junction properties. By virtue of selecting the correct dye, the opportunity is provided for target binding specificity or enhancement of the laser energy. Different dyes would be used for different operations. For example, if a nerve operation was to be performed, dye A would be used. If a blood vessel operation was to be performed, dye B would be used. A dye would be selected which has unique binding affinities for the preferred substrate to be laser-affected. A dye that stains plaque may be desired for one application, a dye that stains glial cells for another application, a dye that stains muscle for yet another application, etc.. It will be appreciated that a dye may be selected for its unique binding affinities for the particular tissue desired to be affected by the laser energy. A dye may also be selected solely for the optical absorption spectrum of the particular dye. It will also be appreciated that the dye could be combined with a surfactant that would actually diffuse down through the tissue and carry the dye with it so that the laser energy would be absorbed by the dye which is below the surface tissue and the surface or overlying tissue would not appreciably absorb the laser energy.

Together with the various different dyes, there are a number of different embodiments and methods of use available with the present invention. An ejection head or heads 10 can be used with a CW (continuous wave) laser, a shuttered CW laser or a pulsed laser.

For the embodiment comprising the CW laser 66 and the ejection head 10, it would be possible to flood the tissue 64, selected for surgery, with a CW laser 66 having a wavelength whose energy was not absorbed by the selected tissue 64 without the presence of a dye 70. Drops 80 of a particular dye 70, which has an optical absorption spectrum which includes that of the wavelength of the CW laser 66, would then be ejected through space by ejection head 10 to be delivered to the tissue 64 in the desired pattern and quantity to perform the desired surgery. The laser energy is then only absorbed by the tissue 64 at the location or locations where the drops 80 of dye 70 are delivered. It could be thought of as doing laser surgery with drops of dye. It will be appreciated that the drops 80 of dye 70 may be ejected in a continuous stream of drops 80 by ejection head 10.

It will also be appreciated that the desired pattern and quantity of drops 80 of dye 70 could be delivered to the selected tissue 64 as the first step and then the selected tissue 64 could be flooded with the energy from the CW laser 66 with the same end result of surgery occurring only where the drops 80 of dye 70 had been delivered to the tissue 64.

For the embodiment comprising the shuttered CW laser and the ejection head 10, it would be possible to use a CW laser having a wavelength whose energy is partially absorbed by the tissue 64 without the presence of a dye 70 and with a shutter mechanism in position to block the laser beam of radiated energy from the CW laser to the tissue 64 when in the closed position and to allow the radiated energy to reach the tissue 64 in the open position. In this embodiment, the shutter would only be opened during the time the drops 80 of dye 70 were being ejected onto the tissue 64. It will be appreciated that the desired pattern and quantity of drops 80 of dye 70 could be delivered to the tissue as the first step and then the shutter could be opened for a predetermined time.

For the embodiment comprising the pulsed laser 66 and the ejection head 10 with the capability of being able to control and vary the pulsing of the ejection head 10 and the pulsed laser 66, many combinations and variations are available. For instance, the ejection head or microjet 10 could be activated before the surgical pulsed laser 66 so the drop or drops 80 of liquid dye 70 would arrive on the tissue 64, where the visible spot of light from the low power laser 62 is positioned, before the short burst of laser energy from the surgical pulsed laser 66 arrived on the tissue 64. For example, the drop 80 of liquid dye 70 could arrive, where the visible spot of light is positioned, more than ten microseconds before the laser energy from the pulsed laser 66 arrives, less than ten microseconds before the laser energy from the pulsed laser 66 arrives or substantially at the same time as the laser energy from the surgical pulsed laser 66 arrives.

It would be possible to deposit multiple drops 80 of liquid dye 70 onto the spot of tissue 64 for each single pulse of laser energy delivered to the same spot of tissue by the pulsed laser 66. It would also be possible to deliver multiple pulses of laser energy to the spot of tissue 64 for each single drop 80 of dye 70 deposited to the same spot of tissue 64.

It will be appreciated that the present invention provides a pulse-controlled dye delivery system combined with a pulsed-type surgical laser and a low power laser, for pointing purposes, to provide for more precision placement and control of the delivery of laser energy during surgery.

Although the present invention has been described with reference to a presently preferred embodiment, it will be appreciated by those skilled in the art that various modifications, alternatives, variations, etc., may be made without departing from the spirit and scope of the invention as defined in the appended claims.

We claim:

1. A method for providing greater precision placement and control of the delivery of laser energy during laser surgery performed on tissue, said method comprising the steps of:
    providing a light source which provides a visible spot of light on the tissue, said visible spot of light to be used as a pointer;
    providing a surgical laser to deliver laser energy in a predetermined band of wavelengths to be used in performing the surgery on the tissue;
    providing a liquid dye having a predetermined optical absorption spectrum which includes the predetermined band of wavelengths of said surgical laser;
    providing at least one ejection head capable of ejecting drops of a liquid dye through space with the diameter of each drop being less than two hundred microns;
    aligning the at least one ejection head such that ejected drops of liquid dye will be delivered to the tissue where the visible spot of light is positioned;
    aligning the surgical laser such that the laser energy therefrom will be delivered to the tissue where the visible spot of light is positioned;
    activating said ejection head at a predetermined time causing a predetermined number of drops of liquid dye to be emitted and delivered through space to the location on the tissue where the visible spot of light is positioned; and
    activating said surgical laser at a different predetermined time causing laser energy to be emitted and delivered to the location on the tissue where the visible spot of light is positioned.

2. The method of claim 1 further including the steps of:

moving said visible spot of light to a different location on the tissue;

activating said ejection head at a predetermined time causing a predetermined number of drops of liquid dye to be emitted and delivered through space to the location on the tissue where the visible spot of light is positioned; and activating said surgical laser at a different predetermined time causing laser energy to be emitted and delivered to the location on the tissue where the visible spot of light is positioned.

3. The method of claim 2 further including the steps of:

repeating the three steps set forth in claim 2 until said laser surgery is completed.

4. The method of claim 1 further providing the steps of:

providing a microscope; and observing the tissue, where the visible spot of light is positioned, through the microscope.

5. The method of claim 1 wherein said surgical laser is a pulsed laser.

6. The method of claim 5 wherein said different predetermined time of activating said surgical laser occurs after said predetermined time of activating said ejection head such that said predetermined number of drops of liquid dye arrives, on the tissue where the visible spot of light is positioned, before said laser energy comprising a predetermined number of pulses of laser energy from said pulsed laser arrives on the tissue where the visible spot of light is positioned.

7. The method of claim 6 wherein said predetermined number of drops of liquid dye comprises one drop and the predetermined number of pulses of laser energy comprises one pulse.

8. The method of claim 6 wherein said predetermined number of drops of liquid dye comprises more than one drop and the predetermined number of pulses of laser energy comprises one pulse.

9. The method of claim 6 wherein said predetermined number of drops of liquid dye comprises one drop and the predetermined number of pulses of laser energy comprises more than one pulse.

10. The method of claim 6 wherein said predetermined number of drops of liquid dye comprises more than one drop and the predetermined number of pulses of laser energy comprises more than one pulse.

11. The method of claim 5 wherein said different predetermined time of activating said surgical laser occurs substantially simultaneously with said predetermined time of activating said ejection head such that each drop of said predetermined number of drops of liquid dye arrives, on the tissue where the visible spot of light is positioned, substantially simultaneously with each pulse of said laser energy comprising a predetermined number of pulses of laser energy from said pulsed laser that arrives on the tissue where the visible spot of light is positioned.

12. The method of claim 11 wherein said predetermined number of drops of liquid dye comprises one drop and the predetermined number of pulses of laser energy comprises one pulse.

13. The method of claim 11 wherein said predetermined number of drops of liquid dye comprises more than one drop and the predetermined number of pulses of laser energy comprises more than one pulse.

14. The method of claim 1 wherein said surgical laser is a continuous wave laser.

15. The method of claim 14 wherein said different predetermined time of activating said surgical laser occurs after said predetermined time of activating said ejection head such that said predetermined number of drops of liquid dye arrives, on the tissue where the visible spot of light is positioned, before said laser energy comprising a continuous wave of laser energy from said continuous wave laser arrives on the tissue where the visible spot of light is positioned.

16. The method of claim 15 wherein said predetermined number of drops of liquid dye comprises one drop.

17. The method of claim 15 wherein said predetermined number of drops of liquid dye comprises more than one drop.

18. The method of claim 14 wherein said different predetermined time of activating said surgical laser occurs before said predetermined time of activating said ejection head such that said predetermined number of drops of liquid dye arrives, on the tissue where the visible spot of light is positioned, after said laser energy comprising a continuous wave of laser energy from said continuous wave laser arrives on the tissue where the visible spot of light is positioned.

19. The method of claim 18 wherein said predetermined number of drops of liquid dye comprises one drop.

20. The method of claim 18 wherein said predetermined number of drops of liquid dye comprises more than one drop.

21. The method of claim 1 wherein said surgical laser is a shuttered continuous wave laser.

22. The method of claim 21 wherein said different predetermined time of activating said surgical laser occurs after said predetermined time of activating said ejection head such that said predetermined number of drops of liquid dye arrives, on the tissue where the visible spot of light is positioned, before said laser energy comprising a continuous wave of laser energy from said shuttered continuous wave CW laser arrives on the tissue where the visible spot of light is positioned.

23. The method of claim 22 wherein said predetermined number of drops of liquid dye comprises one drop.

24. The method of claim 22 wherein said predetermined number of drops of liquid dye comprises more than one drop.

25. The method of claim 21 wherein said different predetermined time of activating said surgical laser occurs before said predetermined time of activating said ejection head such that said predetermined number of drops of liquid dye arrives, on the tissue where the visible spot of light is positioned, after said laser energy comprising a continuous wave of laser energy from said shuttered continuous wave laser arrives on the tissue where the visible spot of light is positioned.

26. The method of claim 25 wherein said predetermined number of drops of liquid dye comprises one drop.

27. The method of claim 25 wherein said predetermined number of drops of liquid dye comprises more than one drop.

28. The method of claim 1 wherein said liquid dye includes a surfactant that would diffuse down through the tissue and carry the liquid dye down through the tissue.

29. The method of claim 1 wherein said laser energy from said surgical laser is delivered through fiber optics.

30. The method of claim 1 wherein said low power laser, said surgical laser and said at least one ejection head are provided in a hand-held unit.

31. The method of claim 1 wherein said laser energy from said low power laser is delivered through fiber optics.

32. The method of claim i further including the steps of:
providing at least one additional ejection head capable of ejecting drops of a wash fluid through space with the diameter of each drop being less than two hundred microns, and
aligning the at least one additional ejection head such that the ejected drops of wash fluid will be delivered through space to the tissue where the visible spot of light is positioned.

33. The method of claim 32 wherein said low power laser, said surgical laser, said at least one ejection head and said at last one additional ejection head are provided in a hand-held unit.

34. The method of claim 1 wherein said light source comprises a low power laser.

35. Apparatus for providing greater precision placement and control of the delivery of laser energy during laser surgery performed on tissue, said apparatus comprising:
a light source which provides a visible spot of light on the tissue, said visible spot of light to be used as a pointer;
a surgical laser to deliver laser energy in a predetermined band of wavelengths to be used in performing the surgery on the tissue, said surgical laser being positioned and aligned with respect to said light source such that the laser energy therefrom will be delivered to the location on the tissue where the visible spot of light from said light source is positioned when said surgical laser is activated;
at least one ejection head capable of ejecting drops of liquid dye through space with the diameter of each drop being less than two hundred microns, said dye being responsive to the wavelength of energy delivered by said surgical laser, said at least one ejection head being positioned and aligned with respect to said light source such that drops of dye ejected from said at least one ejection head will be delivered through space to the location on the tissue where the visible spot of light from said light source is positioned when said at least one ejection head is activated; and
means operatively connected to said surgical laser and said at least one ejection head for activating said surgical laser and said at least one ejection head.

36. The apparatus of claim 35 wherein said means for activating said surgical laser and said at least one ejection head includes means to control the relative time of activation of said surgical laser and said ejection head so the relative time of arrival of the drops of dye and the laser energy from said surgical laser can be controlled and adjusted.

37. The apparatus of claim 36 further including a microscope capable of observing the tissue where the visible spot of light is positioned and structured to hold said low power laser, said surgical laser and said at least one ejection head.

38. The apparatus of claim 37 wherein said microscope includes positioning controls to cause said visible spot of light to move to a different location on said tissue.

39. The apparatus of claim 38 wherein said surgical laser is a pulsed laser.

40. The apparatus of claim 39 wherein said surgical laser is a continuous wave laser.

41. The apparatus of claim 40 wherein said surgical laser is a shuttered continuous wave laser.

42. The apparatus of claim 40 wherein said low power laser, said surgical laser and said at least one ejection head are operatively mounted in a hand-held unit.

43. The apparatus of claim 42 wherein said laser energy from said low power laser is delivered through fiber optics.

44. The apparatus of claim 43 wherein said laser energy from said surgical laser is delivered through fiber optics.

45. The apparatus of claim 44 further including at least one additional ejection head capable of ejecting drops of a wash fluid through space with the diameter of each drop being less than two hundred microns, said at least one additional ejection head being positioned and aligned such that ejected drops of wash fluid will be delivered through space to the tissue where the visible spot of light is positioned.

46. The apparatus of claim 34 wherein said light source comprises a low power laser.

* * * * *

UNITED STATES PATENT AND TRADEMARK OFFICE
CERTIFICATE OF CORRECTION

PATENT NO. : 5,092,864
DATED : March 3, 1992
INVENTOR(S) : Donald J. Hayes, et al.

It is certified that error appears in the above-identified patent and that said Letters Patent is hereby corrected as shown below:

Column 8, line 40, after "wave" delete ---CW---
Column 9, line 7, change "claim i" to read ---claim 1---

Signed and Sealed this

First Day of June, 1993

Attest:

MICHAEL K. KIRK

Attesting Officer         Acting Commissioner of Patents and Trademarks